(12) United States Patent
Daniel et al.

(10) Patent No.: US 12,085,272 B2
(45) Date of Patent: Sep. 10, 2024

(54) LIGHTING SYSTEM WITH VACUUM INTAKE

(71) Applicant: RenO2blu Inc., Moncton (CA)

(72) Inventors: Nachaat Daniel, Dieppe (CA); Michael Martin Dixson, Upper Coverdale (CA)

(73) Assignee: RenO2blu Inc.

( * ) Notice: Subject to any disclaimer, the term of this patent is extended or adjusted under 35 U.S.C. 154(b) by 0 days.

(21) Appl. No.: 17/927,850

(22) PCT Filed: Jun. 2, 2021

(86) PCT No.: PCT/CA2021/050751
§ 371 (c)(1),
(2) Date: Nov. 25, 2022

(87) PCT Pub. No.: WO2021/243455
PCT Pub. Date: Dec. 9, 2021

(65) Prior Publication Data
US 2023/0204204 A1    Jun. 29, 2023

(51) Int. Cl.
| | |
|---|---|
| F21V 33/00 | (2006.01) |
| A61B 90/30 | (2016.01) |
| A61B 90/35 | (2016.01) |
| B08B 15/02 | (2006.01) |
| F21V 21/02 | (2006.01) |
| F21V 21/30 | (2006.01) |
| F21V 23/00 | (2015.01) |
| F21W 131/20 | (2006.01) |
| F24F 13/078 | (2006.01) |

(52) U.S. Cl.
CPC .......... *F21V 33/0088* (2013.01); *A61B 90/35* (2016.02); *B08B 15/02* (2013.01); *F21V 23/002* (2013.01); *F24F 13/078* (2013.01); *A61B 2090/309* (2016.02); *F21V 21/02* (2013.01); *F21V 21/30* (2013.01); *F21W 2131/20* (2013.01)

(58) Field of Classification Search
CPC .... F21V 33/0088; F21V 23/002; F21V 21/02; F21V 21/30; A61B 90/35; A61B 2090/309; A61B 90/30; B08B 15/02; B08B 15/002; F24F 13/078; F24F 7/065; F21W 2131/20
See application file for complete search history.

(56) References Cited

U.S. PATENT DOCUMENTS

| | | |
|---|---|---|
| 4,109,144 A | 8/1978 | Vidmar |
| 4,860,644 A | 8/1989 | Kohl |
| (Continued) | | |

FOREIGN PATENT DOCUMENTS

| | | |
|---|---|---|
| DE | 102009060764 A1 | 7/2011 |
| KR | 20040047552 A | 6/2004 |

*Primary Examiner* — Tsion Tumebo
(74) *Attorney, Agent, or Firm* — McMillan LLP

(57) ABSTRACT

A lighting system with vacuum intake is provided, having a lighting structure including at least one light-emitting element dimensioned to illuminate a region, and a lighting support structure extending at a first end thereof from the lighting structure and enabling repositioning of the lighting structure relative to a second end of the lighting support structure. The lighting support structure hays an air conduit extending therealong and connectable or connected towards the second end of the lighting support structure to a vacuum system, the air conduit being in fluid communication with a vacuum intake positioned towards the lighting structure.

15 Claims, 13 Drawing Sheets

(56) References Cited

U.S. PATENT DOCUMENTS

| | | | | |
|---|---|---|---|---|
| 4,926,293 | A * | 5/1990 | Saba | E04H 3/04 |
| | | | | 362/345 |
| 5,336,130 | A * | 8/1994 | Ray | B08B 15/002 |
| | | | | 454/65 |
| 5,427,569 | A * | 6/1995 | Plymoth | B08B 15/002 |
| | | | | 454/65 |
| 6,395,047 | B1 * | 5/2002 | Smith | F24F 8/10 |
| | | | | 55/385.2 |
| 6,503,139 | B2 * | 1/2003 | Coral | F16L 27/0861 |
| | | | | 454/67 |
| 6,974,375 | B1 | 12/2005 | Stevenson | |
| 8,892,222 | B2 * | 11/2014 | Simms | B23K 9/325 |
| | | | | 700/62 |
| 9,615,884 | B2 * | 4/2017 | Armour | A61L 2/06 |
| 10,072,869 | B2 * | 9/2018 | Zakula | F24F 13/078 |
| 11,298,564 | B2 * | 4/2022 | Anderson | A61N 5/0624 |
| 11,383,000 | B2 * | 7/2022 | Botts | A61L 9/20 |
| 2010/0234794 | A1 * | 9/2010 | Weadock | A61G 13/108 |
| | | | | 604/23 |
| 2013/0052928 | A1 * | 2/2013 | Wolfhagen | B08B 15/002 |
| | | | | 454/63 |
| 2016/0100095 | A1 * | 4/2016 | Weingard | A61B 90/30 |
| | | | | 348/345 |
| 2019/0049045 | A1 * | 2/2019 | Stenberg | F16L 43/02 |

* cited by examiner

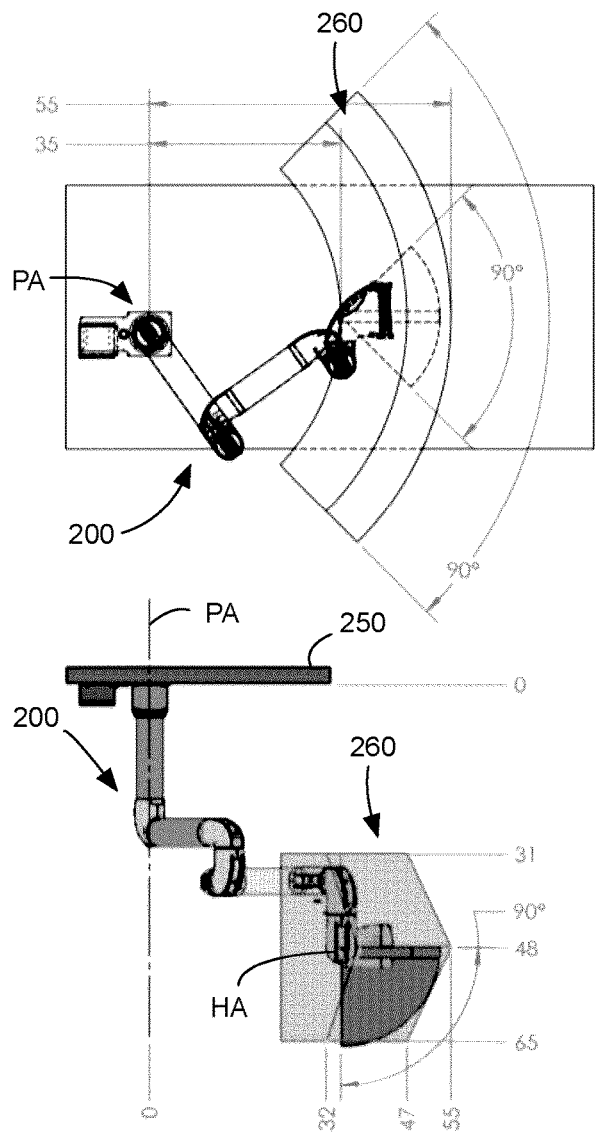
FIG. 12A
FIG. 12B
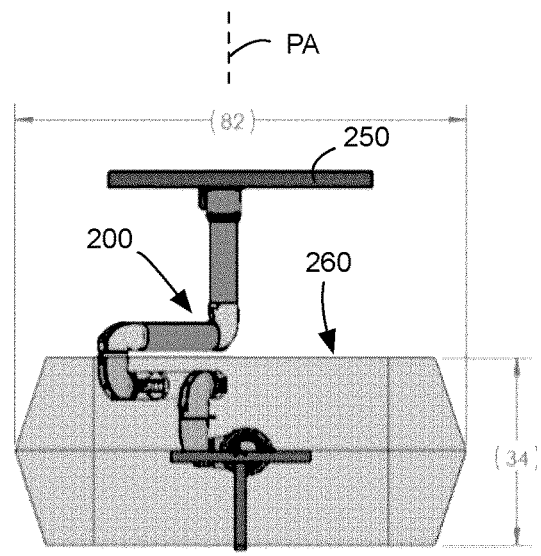
FIG. 12C

LIGHTING SYSTEM WITH VACUUM INTAKE

CROSS-REFERENCE TO RELATED APPLICATIONS

This application claims the benefit of U.S. Provisional Application No. 63/033,692, filed Jun. 2, 2020, the contents of which are incorporated herein by reference in their entirety.

FIELD

The specification relates generally to a lighting system and, in particular, to a light system with vacuum intake.

BACKGROUND OF THE DISCLOSURE

The outbreak of CoViD-19 has increased the risks of healthcare workers treating patients. CoViD-19 is a virus that appears to be transmitted primarily via airborne secretions and aerosols emanating from the oral and nasal cavities. This is particularly true for treatment of a patient who is undergoing an oral or facial procedure. During oral and facial procedures, such as, for example, dentistry, ENT, plastic surgery, and ophthalmology, it is very difficult to restrict secretions emanating from the patient from being exhaled into the immediate vicinity of the patient's mouth and/or nose.

SUMMARY OF THE DISCLOSURE

In one aspect, there is provided a lighting system with vacuum intake, comprising: a lighting structure including at least one light-emitting element dimensioned to illuminate a region; and a lighting support structure extending at a first end thereof from the lighting structure and enabling repositioning of the lighting structure relative to a second end of the lighting support structure, the lighting support structure having an air conduit extending therealong and connectable or connected towards the second end of the lighting support structure to a vacuum system, the air conduit being in fluid communication with a vacuum intake positioned towards the lighting structure.

The at least one light-emitting element can incude at least one light-emitting diode.

The lighting structure can be positioned to at least partially surround the vacuum intake. The lighting structure can fully surround the vacuum intake.

The lighting system with vacuum intake can further include a vacuum system in fluid communication with the air conduit towards the second end of the lighting support structure.

The lighting system with vacuum intake can further include an electrical wiring guide system positioned within the air conduit to guide electrical wiring from the lighting structure through the lighting support structure.

The lighting system with vacuum intake can further include an articulation damping system connected to the lighting support structure to resist articulation of the lighting support structure.

The articulation damping system can be positioned in the air conduit of the lighting support structure.

The lighting support structure can include at least two support structure segments, and a rotational joint between a first of the at least two support structure segments and a second of the at least two support structure segments.

The lighting system with vacuum intake can further include an articulation damping system connected to the lighting support structure to resist articulation of the first of the at least two support structure segments and the second of the at least two support structure segments. The articulation damping system can be positioned in the air conduit of the lighting support structure. The lighting system can further include an electrical guide system positioned within the air conduit to guide electrical wiring from the lighting structure through the lighting support structure.

The lighting system with vacuum intake can further include a booster fan positioned within the lighting support structure.

The lighting system with vacuum intake can further include a bag filter fitted within the vacuum intake.

Other technical advantages may become readily apparent to one of ordinary skill in the art after review of the following figures and description.

BRIEF DESCRIPTIONS OF THE DRAWINGS

For a better understanding of the embodiment(s) described herein and to show more clearly how the embodiment(s) may be carried into effect, reference will now be made, by way of example only, to the accompanying drawings in which:

FIGS. 12A to 12C show the dimensions and operating ranges of the lighting system of FIGS. 5A to 6.

Figure 1:
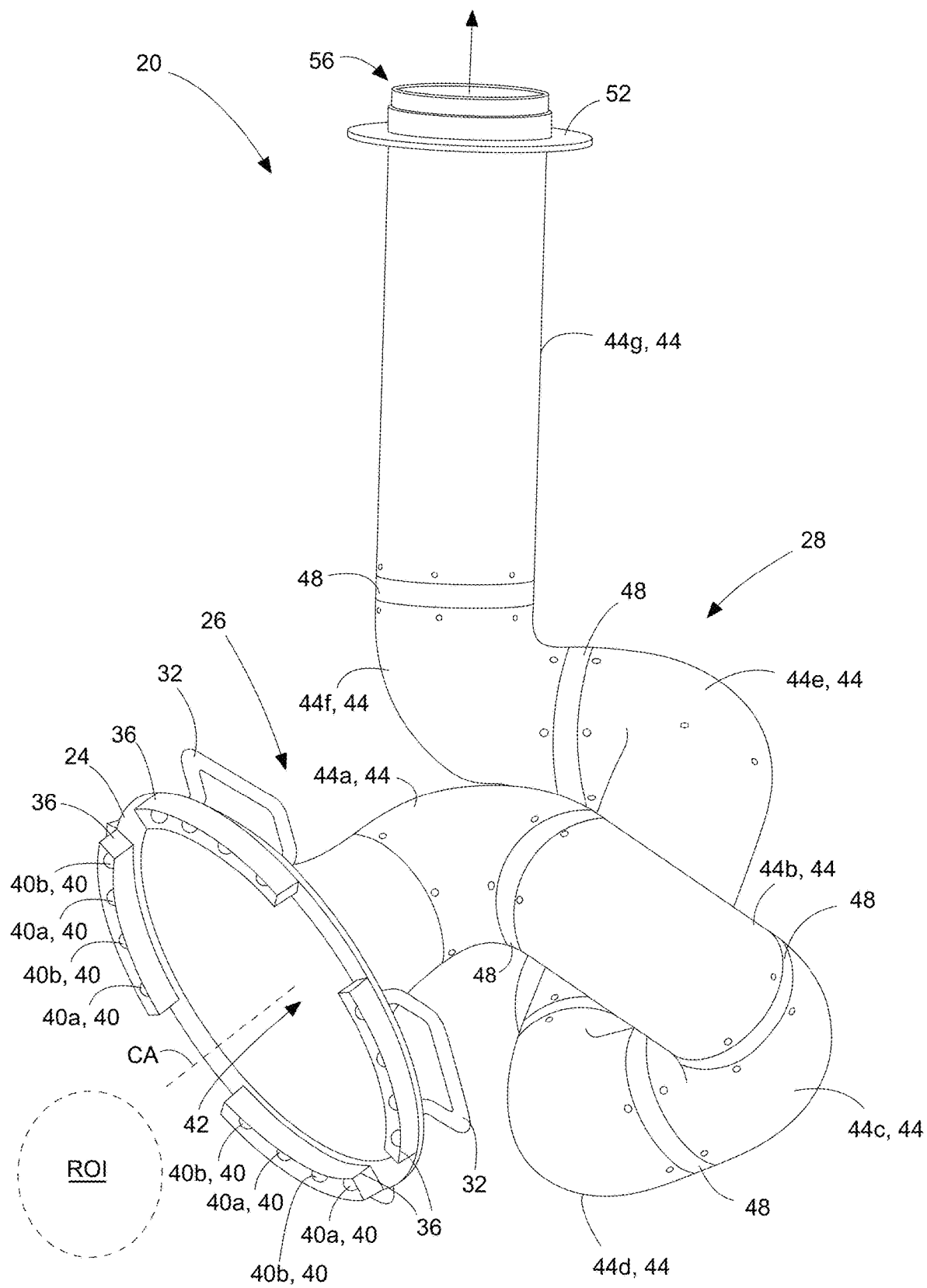
FIG. 1 shows a lighting system in accordance with an embodiment.

Unless otherwise specifically noted, articles depicted in the drawings are not necessarily drawn to scale.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiment or embodiments described herein. However, it will be understood by those of ordinary skill in the art that the embodiments described herein may be practiced without these specific details. In other instances, well-known methods, procedures and components have not been described in detail so as not to obscure the embodiments described herein. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description. It will also be noted that the use of the term "a" or "an" will be understood to denote "at least one" in all instances unless explicitly stated otherwise or unless it would be understood to be obvious that it must mean "one".

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

A lighting system 20 in accordance with an embodiment is shown in FIG. 1. The lighting system 20 is constructed for use in a healthcare facility, such as a surgery room or a dental procedure room for dental or facial surgical procedures (including oral surgery, ENT, and ophthalmology).

The lighting system 20 has a lighting structure 24 that is connected to an intake end 26 of a lighting support structure 28. The lighting structure 24 is shaped like a bell of a brass horn, extending radially from a central axis CA. A set of four handles 32 extend from the lighting structure 24.

The lighting structure 24 is configured/dimensioned to illuminate a region, such as the oral region of a patient. Four lighting strips 36 are positioned on a periphery of the lighting structure 24 and extend at least partially around the periphery. Each of the lighting strips 36 includes one or more light-emitting elements in the form of alternating pairs of white LEDs 40a and yellow LEDs 40b, alternatively collectively referred to hereinafter as LEDs 40. There are thus eight white LEDs 40a and eight yellow LEDs 40b positioned alternatingly about the periphery of the lighting structure 24 to illuminate a region of interest ROI. In other embodiments, the light-emitting elements can be LEDs of a single color or three or more colors, or other suitable illumination sources. The region of interest ROI shown is exemplary, and it will be appreciated that the region of interest can be varied by alternating the positioning of the light-emitting elements.

A vacuum intake 42 of the lighting support structure 28 towards the intake end 26 thereof is positioned centrally in the lighting structure 24. As is shown, the lighting structure 24 at least partially or fully surrounds the vacuum intake 42.

The lighting support structure 28 has an articulating arm that is formed from a set of support structure sections 44a to 44g (alternatively collectively referred to hereinafter as support structure sections 44) that articulate relative to each other at a set of joints 48. The lighting structure 24 is integrally formed with a first support structure section 44a, which extends from the lighting structure 24. The joints 48 are constructed to enable full 360 degree rotation of adjacent pairs of support structure sections 44. In other embodiments, the joints can enable less than full rotation of adjacent pairs of support structure sections 44.

A mounting flange 52 is positioned towards an output end 56 of the lighting support structure 28 opposite the lighting structure 24.

The support structure sections 44 are tubular so that the lighting support structure 28 forms an air conduit from the vacuum intake 42 towards the intake end 26, towards which the lighting structure 24 is positioned, to the output end 56. Each of the support structure sections 44 are molded or otherwise formed unitarily, but can be formed from two or more elements in other embodiments.

Figure 2:
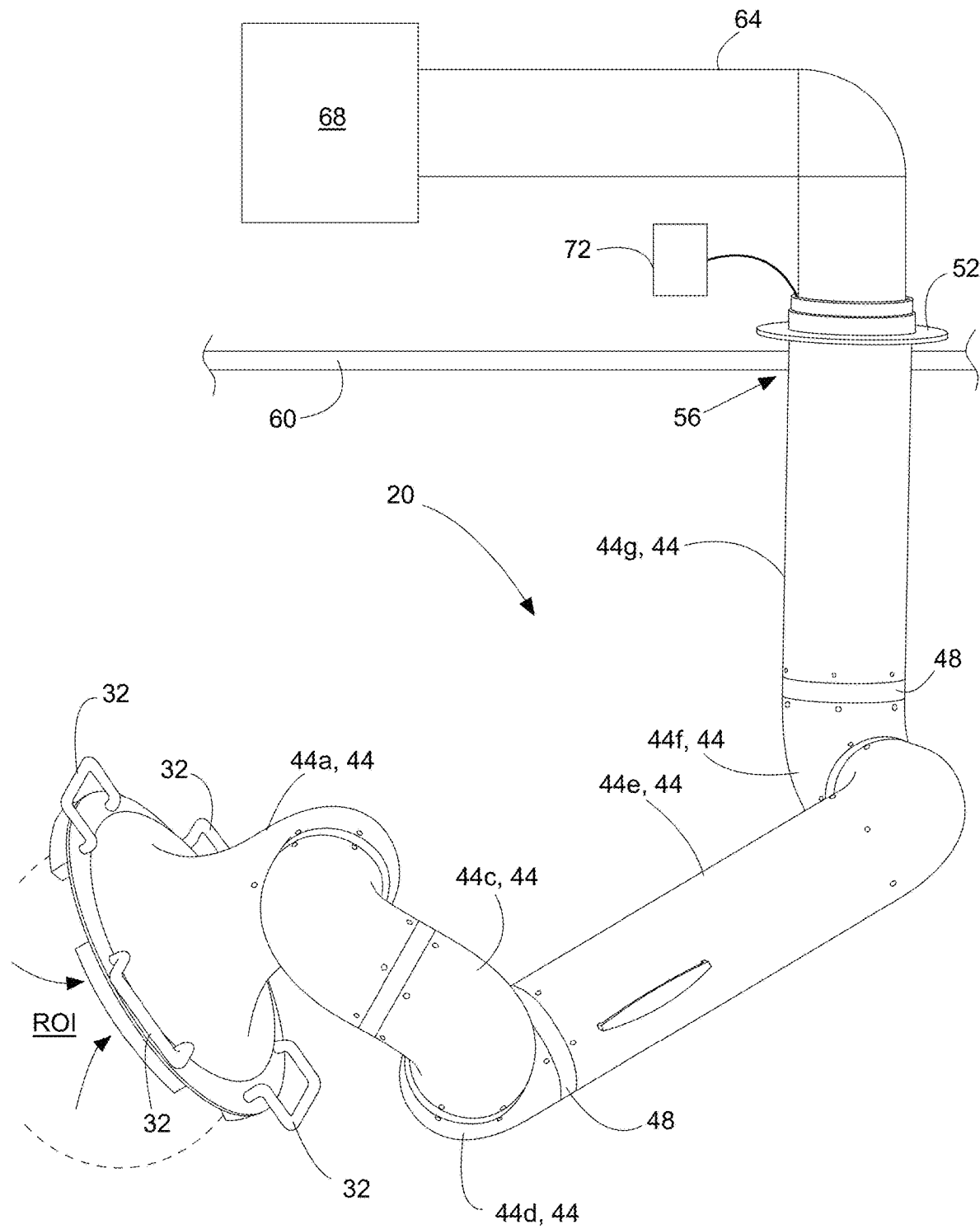
FIG. 2 is a schematic diagram showing the lighting system of FIG. 1 deployed in an environment.

FIG. 2 shows the lighting system 20 installed in an environment. The lighting system 20 is mounted in a ceiling 60, with the flange 52 positioned and secured atop of the ceiling 60 and/or its underlying structure to support the lighting system 20. As the lighting system 20 is primarily constructed of tubular lightweight polymer, its weight is not a significant stress on the ceiling structure. The output end of the lighting support structure 28 is sealingly coupled to a duct 64 that is, in turn connected to a vacuum filtration system 68. The vacuum filtration system 68 generates a negative pressure to draw air through the air conduit of the lighting support structure 28 from the vacuum intake 42 to draw in ambient air from the region of interest ROI.

The lighting support structure 28 includes an electrical guide system including a set of electrical guides extending internally along its length to guide electrical wiring coupled to the LEDs 40a, 40b internally through the lighting support structure 28 to an electrical power supply 72, such as an electrical outlet. In other embodiments, power can be provided to the light-emitting elements in other ways, such as electrical wiring extend outside of the lighting support structure 28 to a power supply, or via one or more battery packs.

The bent shape of a number of the support structure sections 44 combined with the full rotation afforded by the joints 48 enable reorientation and repositioning of the lighting structure 24 via manipulation of the handles 32.

Figure 3:
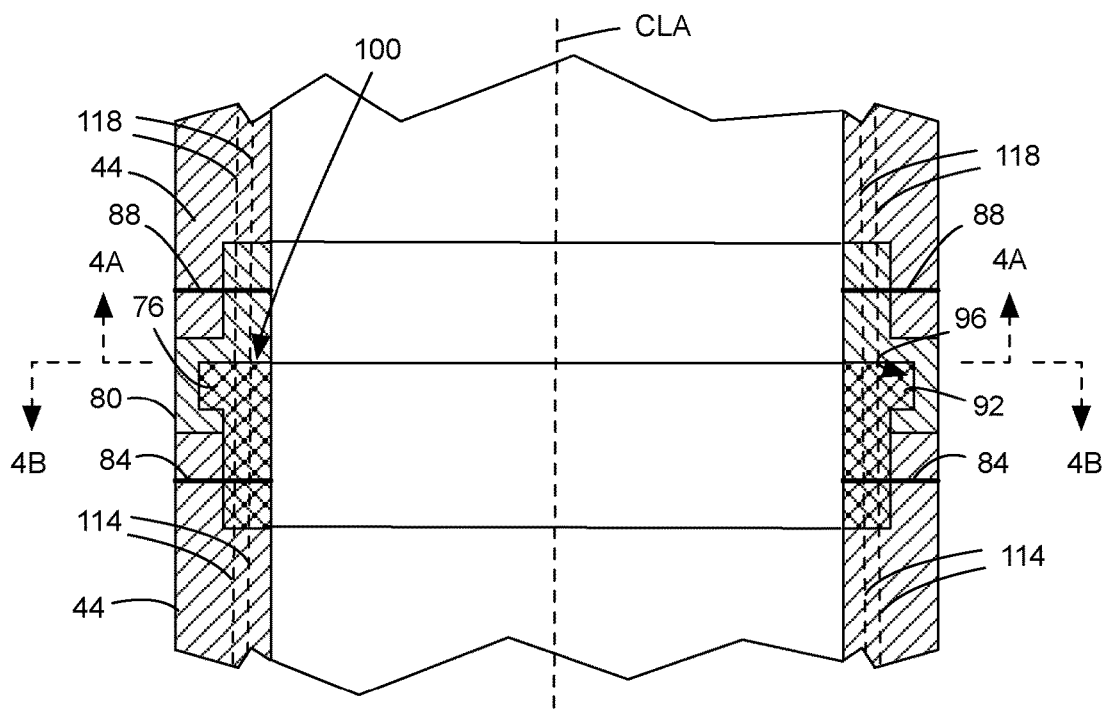
FIG. 3 is a side section view of an articulating joint of a support arm of the lighting system of FIGS. 1 and 2.

FIG. 3 shows a side section view of a joint 48 of the lighting support structure 28. The joint 48 is formed between two support structure sections 44, and includes two annular mating connectors 76, 80. A first annular mating connector 76 is secured to a first of the structural support sections 44 via a set of screws 84 and a second annular mating connector 80 is secured to a second of the structural support sections 44 via a set of screws 88. The first annular mating connector 76 includes an annular flange 92 that is received within an annular channel 96 of the second annular mating connector 80. The annular mating connectors 76, 80 are constructed from or are provided with mating surfaces made of a material that is resistive to abrasion.

Figure 4A:
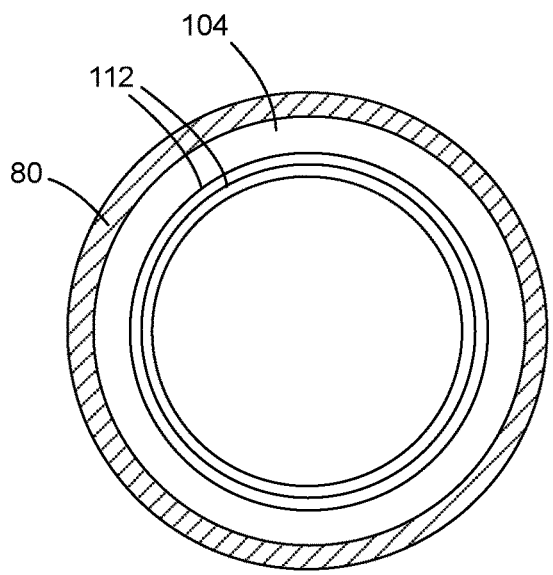
FIG. 4A shows a section view of the articulating joint of FIG. 3 along 4A-4A.
Figure 4B:
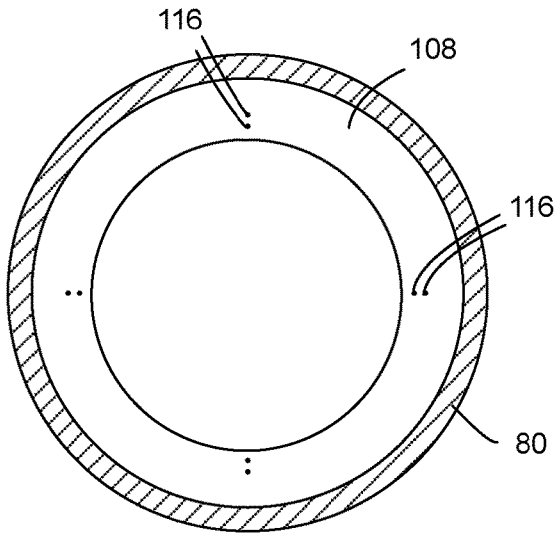
FIG. 4B shows a section view of the articulating joint of FIG. 3 along 4B-4B.

An annular surface interface 100 that is perpendicular to a central longitudinal axis CLA of the support structure sections 44 includes a surface 104 of a lower of the support structure sections 44 shown in FIG. 4A and a surface 108 of an upper of the support structure sections 44 shown in FIG. 4B.

Now with reference to FIGS. 3, 4A, and 4B, a set of annular contact rails 112 along the surface 104 are connected to electrical leads 114 that extend through a sidewall of the lower support structure section 44. Pairs of matching spring-biased pins 116 are positioned along the surface 108 of the upper support structure section 44 and are urged into contact with the annular contact rails 112 when the support structure 28 is assembled. The pins 116 are electrically connected to electrical leads 118 that extend longitudinally through a sidewall of the upper support structure section 44. Multiple redundant sets of the pins 116 inhibit a discontinuity in contact between at least a pair of the pins 116 and the annular contact rails 112.

The support structure sections 44 are sealed at the joints 48 to prevent leakage of air from the air conduit of the lighting support structure 28.

Returning again to FIG. 2, depending on the power of the vacuum filtration system 68, the lighting system 20 has removed as much as 45% of spatter expelled by a patient in the vicinity of the lighting structure 24 when the lighting system was positioned at a distance of 16-18 inches from the head of a patient. In addition, the distance that spatter travelled from the patient's mouth was found to decrease by 40%. Using a Dustrack device to detect aerosols, particles of 1, 2.5, 5, and 10 microns were detected during the dental procedure with and without the lighting system 20. Using the lighting system 20, there was a 45% reduction in the amount of aerosol when the Dustrack was placed 6 feet away from the patient's head. A 75%-90% reduction of aerosol was achieved when the Dustrack was placed beside the head of the patient. These results outline a strong benefit of using the lighting system 20 in reducing aerosol and spatter.

Figure 5A:
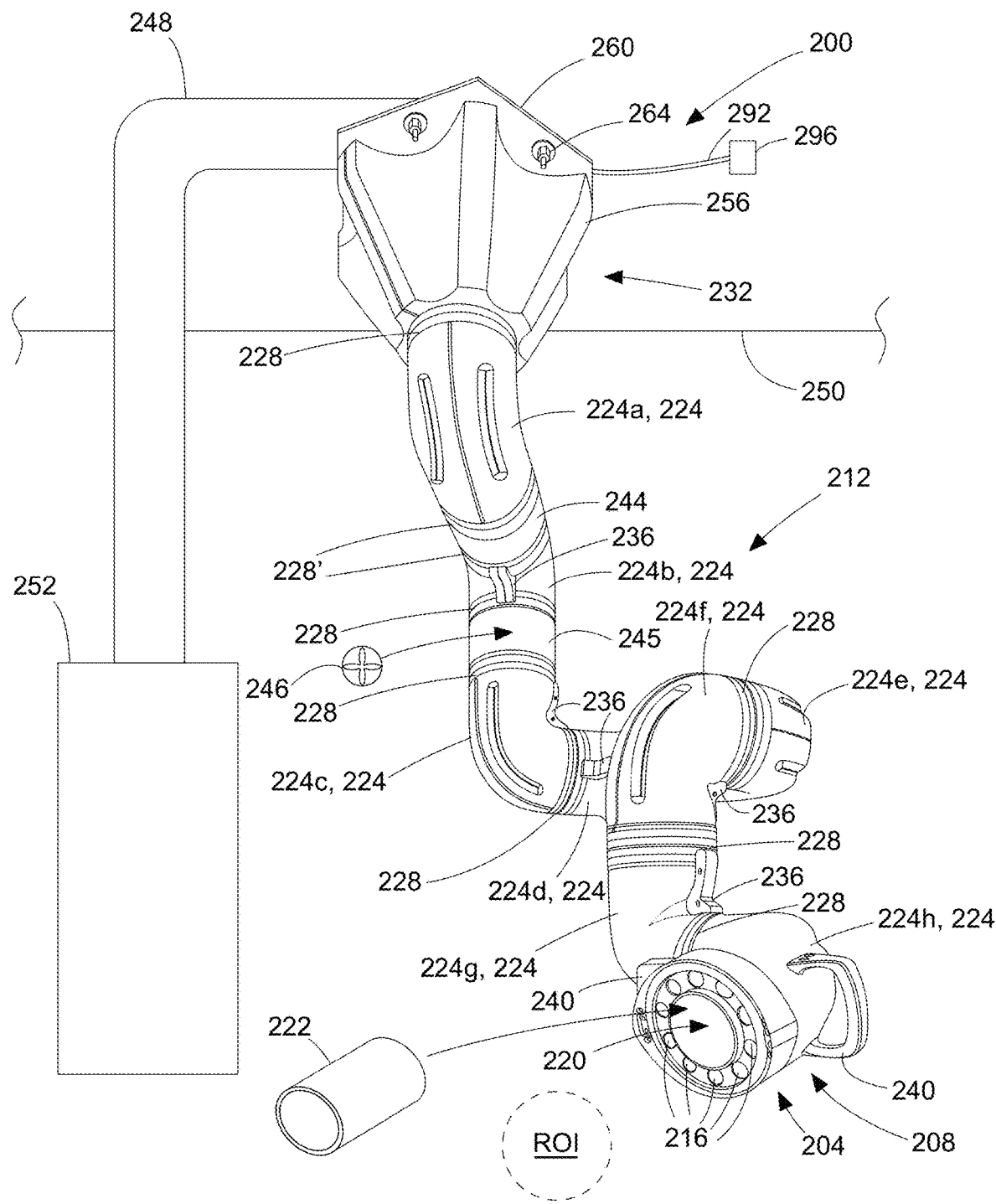
FIGS. 5A to 5B show a lighting system in accordance with another embodiment.
Figure 5B:
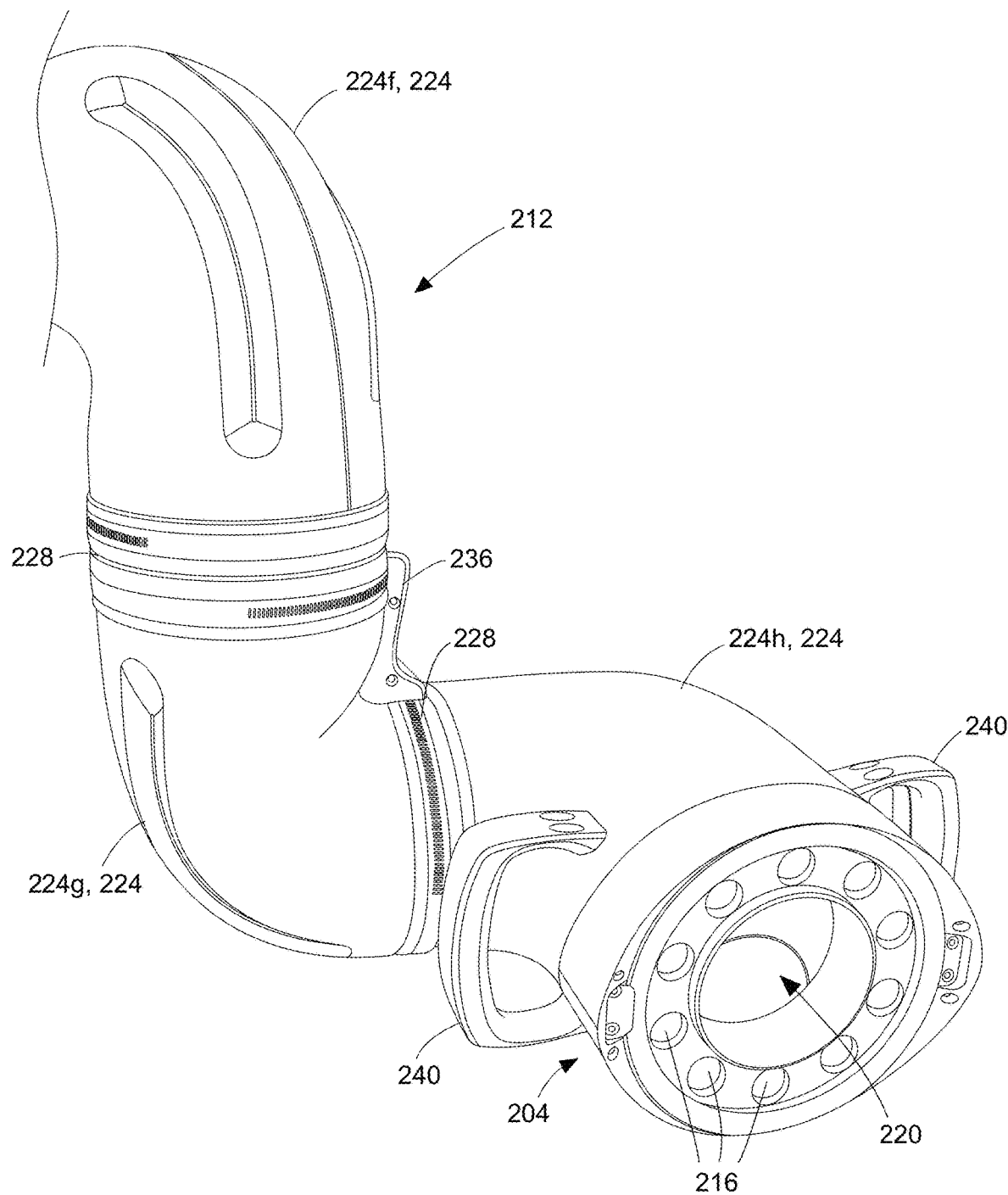

FIGS. 5A and 5B show a lighting system 200 in accordance with another embodiment. The lighting system 200 includes a lighting structure 204 that is connected to an intake end 208 of a lighting support structure 212. The lighting structure 204 in this embodiment has the same profile as the lighting support structure 212. A set of light-emitting diodes (LEDs) 216 are arranged fully surrounding a vacuum intake 220. A disposable/replaceable bag filter 222 is fitted inside the vacuum intake 220 to capture at least some of the aerosols and/or other airborne particles drawn into the vacuum intake 220. The bag filter 222 can be replaced for each patient to reduce the risk of contamination of one patient by a previous patient.

The vacuum intake 220 is dimensioned to generate sufficient suction to draw in most of the air from around a region of interest ROI, such as a patient's mouth. As will be appreciated, by reducing the size of the vacuum intake within a certain range, the lighting system 200 can pull in more of the ambient air in front of the lighting structure 204. The close clustering of the LEDs 216 also better focuses the light generated by the LEDs 216 on the region of interest ROI. The focal length of the lighting is presently 23.6 inches in the present embodiment, but can be varied as needed. Preferably, the linear velocity of the air at the focal length exceeds 14 inches per minute, and is more preferably at least 15 inches per minute. The LEDs 216 can be all of the same type and color, such as 5000 degrees Kelvin, producing about 4000 to 32000 lux that can be manually adjusted or can be of varying colors and/or types, such as alternating colors arranged around the vacuum intake 220. The light pattern generated by the LEDs 216 at the focal length of 23.6 inches is 3.2 inches by 5.5 inches. In other embodiments, the colors, intensities, focal length, and pattern at the focal length can be varied.

The lighting support structure 212 includes an articulating arm that is formed from a set of eight support structure sections 224a to 224h (alternatively collectively referred to hereinafter as support structure sections 224) that articulate relative to each other at a set of joints 228. Of note, however, is that support structure sections 224a and 224b are connected via joints 228' that do not articulate, holding the support structure sections 224a and 224b in fixed orientation relative to one another. The support structure sections 224 are tubular so that the lighting support structure 212 forms an air conduit from the vacuum intake 220 towards the intake end 208, towards which the lighting structure 204 is positioned, to an output end 232 of the lighting support structure 212. The diameter of the support structure sections is about six inches, but can be varied in other embodiments. Each of the support structure sections 224 is elbow-shaped, and the portion of the air conduit therein is likewise diverted 90 degrees from entrance to exit of the support structure section 224. The support structure sections 224 are similarly dimensioned so that their shells can be moulded from a single mould. In this embodiment, the shells of the support structure sections 224 are formed of a lightweight polymer, but can be formed from any other suitable material. Reinforcement members 236 are secured along the inside curve of the exterior surface of support structure sections 224a to 224g to resist bending moments from pulling or pushing of handles 240 secured to the lighting support structure 212 towards the intake end 208 to reposition the lighting structure 204. The joints 228 are constructed to enable full 360 degree rotation of adjacent pairs of support structure sections 224. In order to enable the lighting system to extend as required in various directions while using like-dimensioned support structure sections 224, straight couplers 244, 245 of varying lengths are positioned between some of the support structure sections 224. In other embodiments, the joints can enable less than full rotation of adjacent pairs of support structure sections 224. The output end 232 of the lighting support structure 212 is sealingly connected to an air duct 248 embedded in a ceiling 250 and connects to a vacuum system 252. The vacuum system 252 generates a negative pressure to draw air through the air conduit of the lighting support structure 212 from the vacuum intake 220 to draw in ambient air from the region of interest ROI. In addition, a booster fan 246 is positioned within the straight coupler 245 to assist with the airflow. In other embodiments, the booster fan can be eliminated, or can be augmented with additional booster fans at other locations in the air conduit of the lighting support structure 212.

Figure 6:
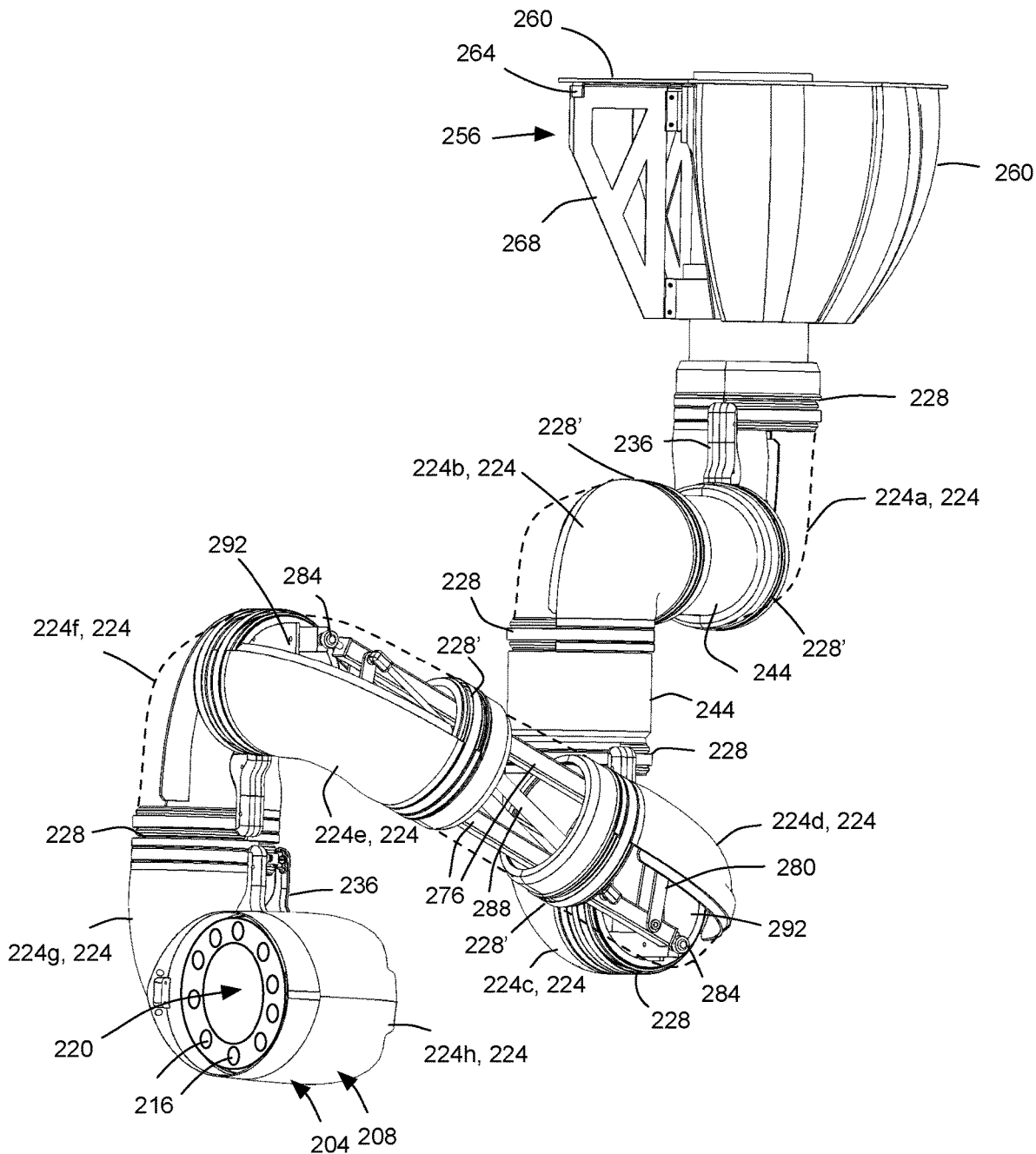
FIG. 6 shows the lighting system of FIGS. 5A to 5B with portions removed to illustrate internal elements.

Now with reference to FIGS. 5A to 6, a mounting structure 256 is positioned towards an output end 232 of the lighting support structure 212 opposite the lighting structure 204 to support the lighting system 200 against bending moments as a result of forces applied to the lighting system 200. A mounting plate 260 of the mounting structure 256 is securable to a structure or frame of the ceiling 250 via a set of fasteners 264, such as bolts. Within a skin 260 of the mounting structure 256 are a set of braces 268 that inhibit bending of the lighting system 200 relative to the air duct 248 positioned within the ceiling 250.

Some of the shell halves of the support structure sections 224 are removed in FIG. 6, showing an articulation damping system 272 that both maintains the generally vertical orientation of portions of the support structure sections 224f and 224g and dampens articulation of the joints 228 to thereby enable the lighting support structure 212 to more readily hold its shape once configured by an operator.

Figure 7:
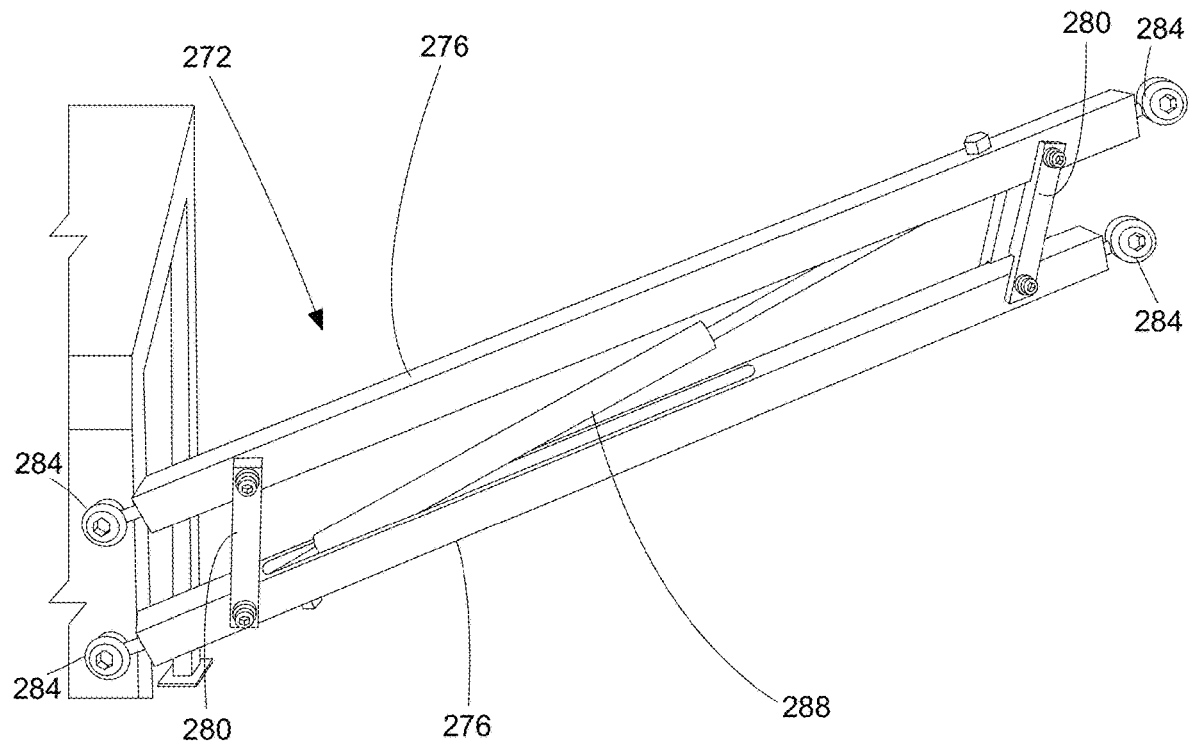
FIG. 7 shows a rotation dampener of the lighting system of FIGS. 5A to 6 in isolation.

The articulation damping system 272 is shown in isolation in FIG. 7, and includes a pair of parallel rods 276 coupled together towards both ends via a pair of cross-members 280. A connector 284 is positioned at each end of each of the pair of parallel rods 276 and is pivotally fastenable to an anchor point. The parallel rods 276 are pivotable about the anchor points and they are maintained parallel to one another via the cross-members 280. A damping element in the form of a gas cylinder 288 is connected to a first of the parallel rods 276 towards a first end and to a second of the parallel rods 276 towards a second end to resist pivoting of the parallel rods 276 relative to the anchor points.

Referring again to FIG. 6, an anchor plate 292 in each of the support structure sections 224c and 22f provides anchor points for connection of the connectors 284 of the articulation damping system 272. The lighting structure 204 can, as a result, be moved upwardly or downwardly as a result of the pivoting of the combination of support structure sections 224d and 224e relative to support structure sections 224c and 224f respectively. Once moved into an orientation, the articulation damping system 272 resists movement of the lighting support structure 212 until a threshold force is applied to overcome the resistance of the articulation damping system 272.

The air conduit within the lighting support structure 212 is dimensioned to enable sufficient suction to pass through the air conduit even with the presence of the electrical wiring and the articulation damping systems 272. Further, the vacuum system 252 is selected to provide sufficient negative pressure to draw in 70% or more of the ambient air in the region of interest ROI.

FIG. 5 shows electrical wiring 292 that extends from the lighting structure 204 and through the lighting support structure 212 emerging from the output end 232 of the lighting support structure 212 and connected to a power supply 296, such as a standard electrical outlet. The electrical wiring 292 is routed internally within the lighting support structure 212.

Figure 8:
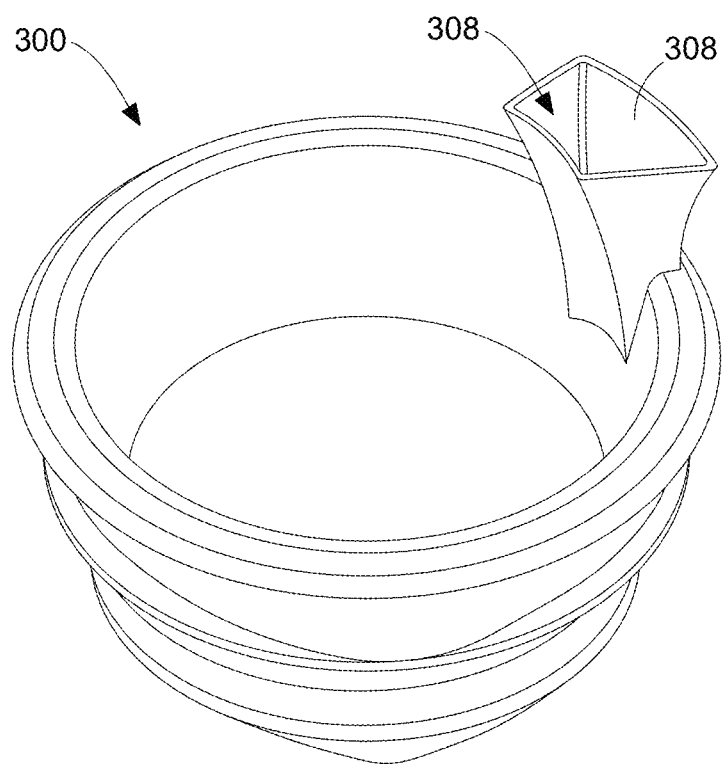
FIG. 8 shows a joint coupler of the lighting support system of the lighting system of FIGS. 5A to 6 having an electrical wiring conduit.

FIG. 8 shows a joint connector 300 over which the support structure sections 224 are fitted. The joint connector 300 includes an electrical wiring guide 304 having a channel 308 through which the electrical wiring 292 is routed. In other embodiments, power can be provided to the light-emitting elements in other ways, such as electrical wiring extend outside of the lighting support structure 28 to a power supply, or via one or more battery packs.

Figure 9:
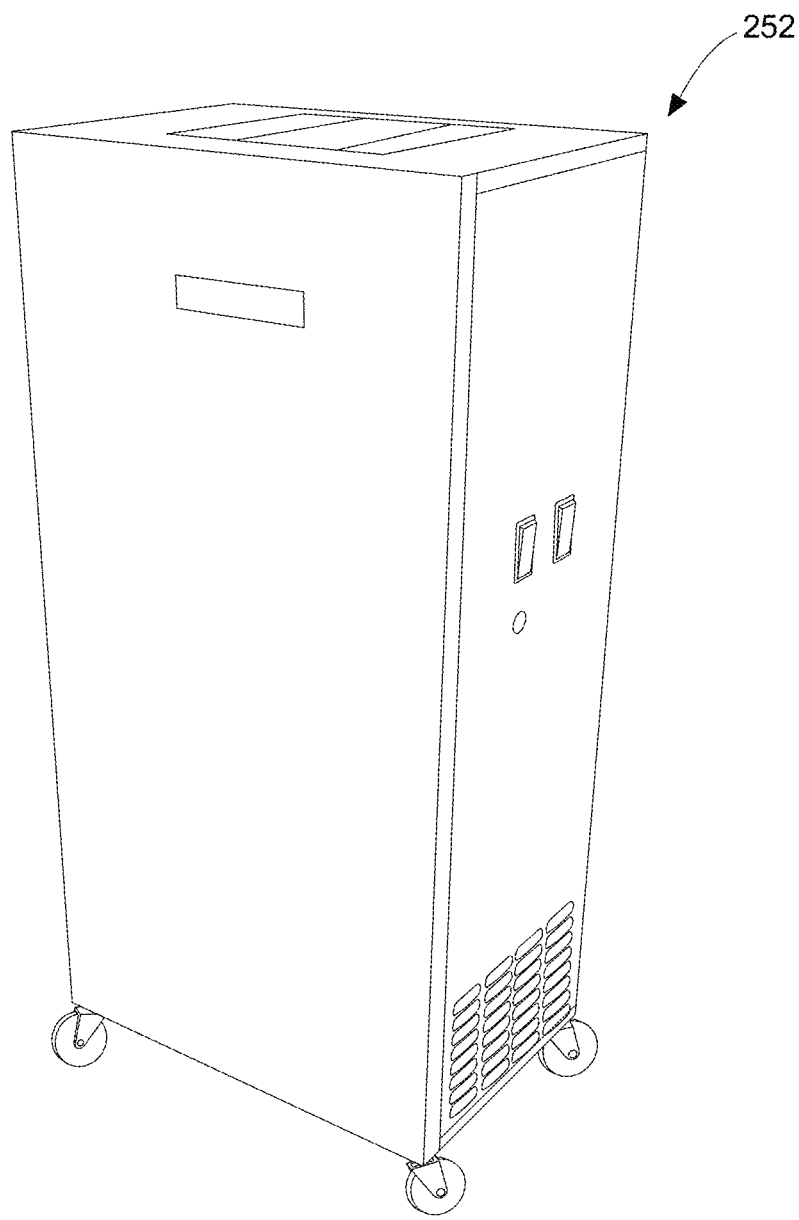
FIG. 9 shows a vacuum system used in combination with the lighting system of FIGS. 5A to 6.

FIG. 9 shows an exemplary commercial vacuum system 252 that can be used in the lighting system 200. Preferably, the vacuum system 252 includes a filtration system for filtering aerosols and other airborne contaminants.

Figure 10A:
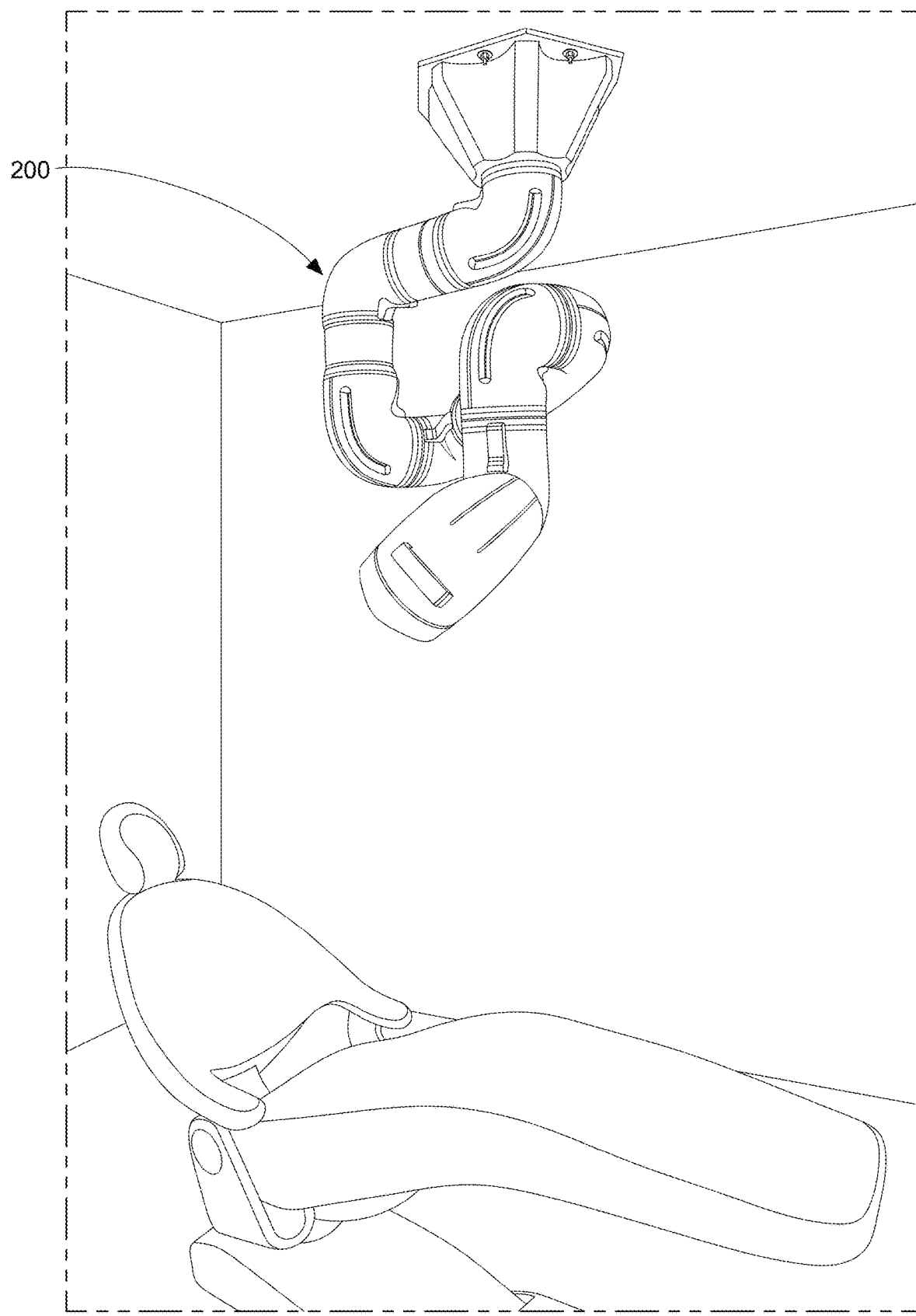
FIG. 10A shows the lighting system of FIGS. 5A to 6 that is ceiling mounted and conditioned in a compact configuration.
Figure 10B:
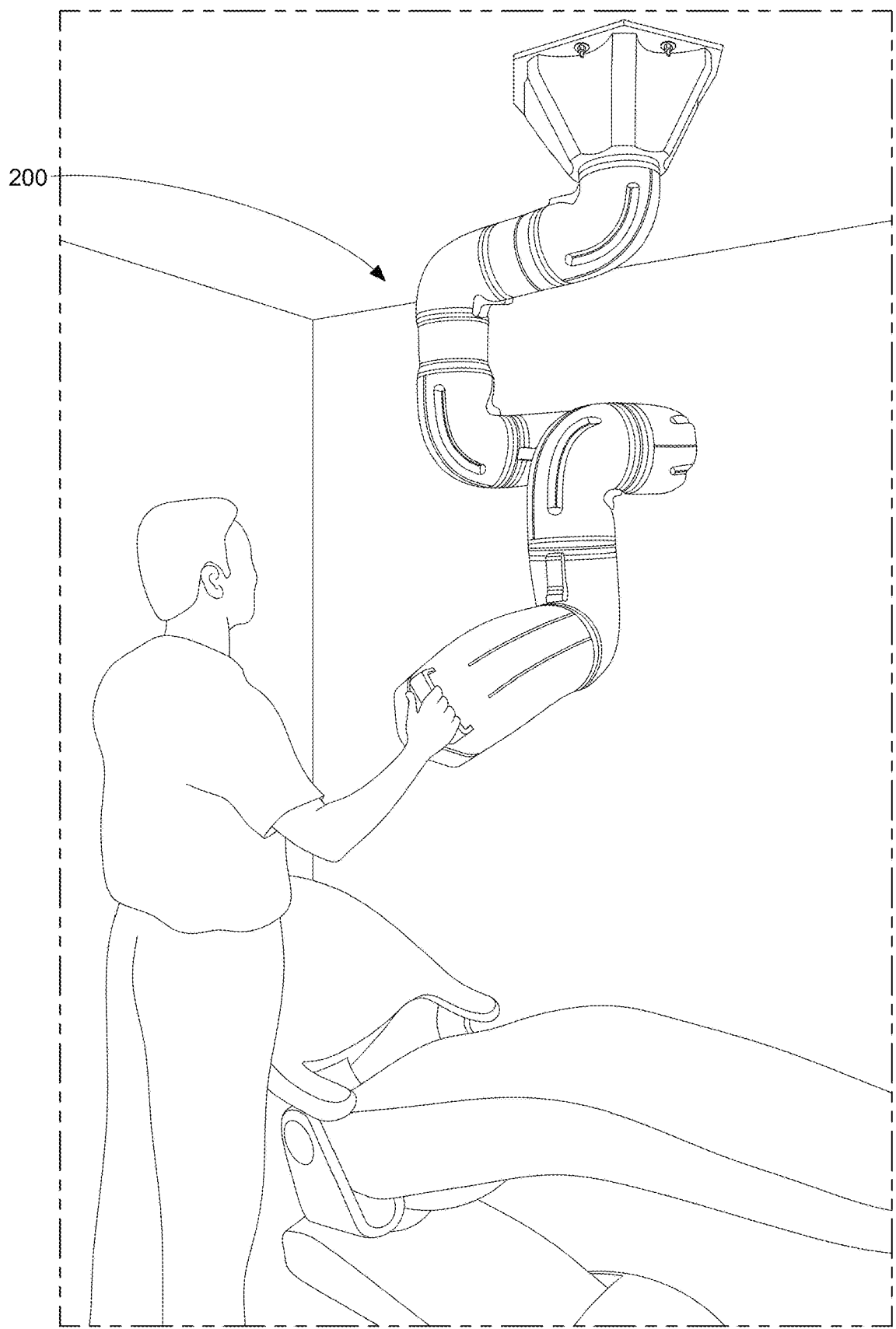
FIG. 10B shows the lighting system of FIG. 10A being positioned by an operator to a use configuration.

FIG. 10A shows the lighting system 200 conditioned to a compact storage state in which the lighting structure is at its highest vertical elevation. The lighting system 200 is designed for a target ceiling height of 102 inches and for a region of interest approximately 44 inches vertically from the ceiling. An operator can then use the handles 240 to pull the lighting structure 204, as shown in FIG. 10B, into a desired position, conditioning the lighting structure into a use state. As a result of the articulation damping system, the lighting structure 204 is stable at any of a continuum of positions.

Figure 11:
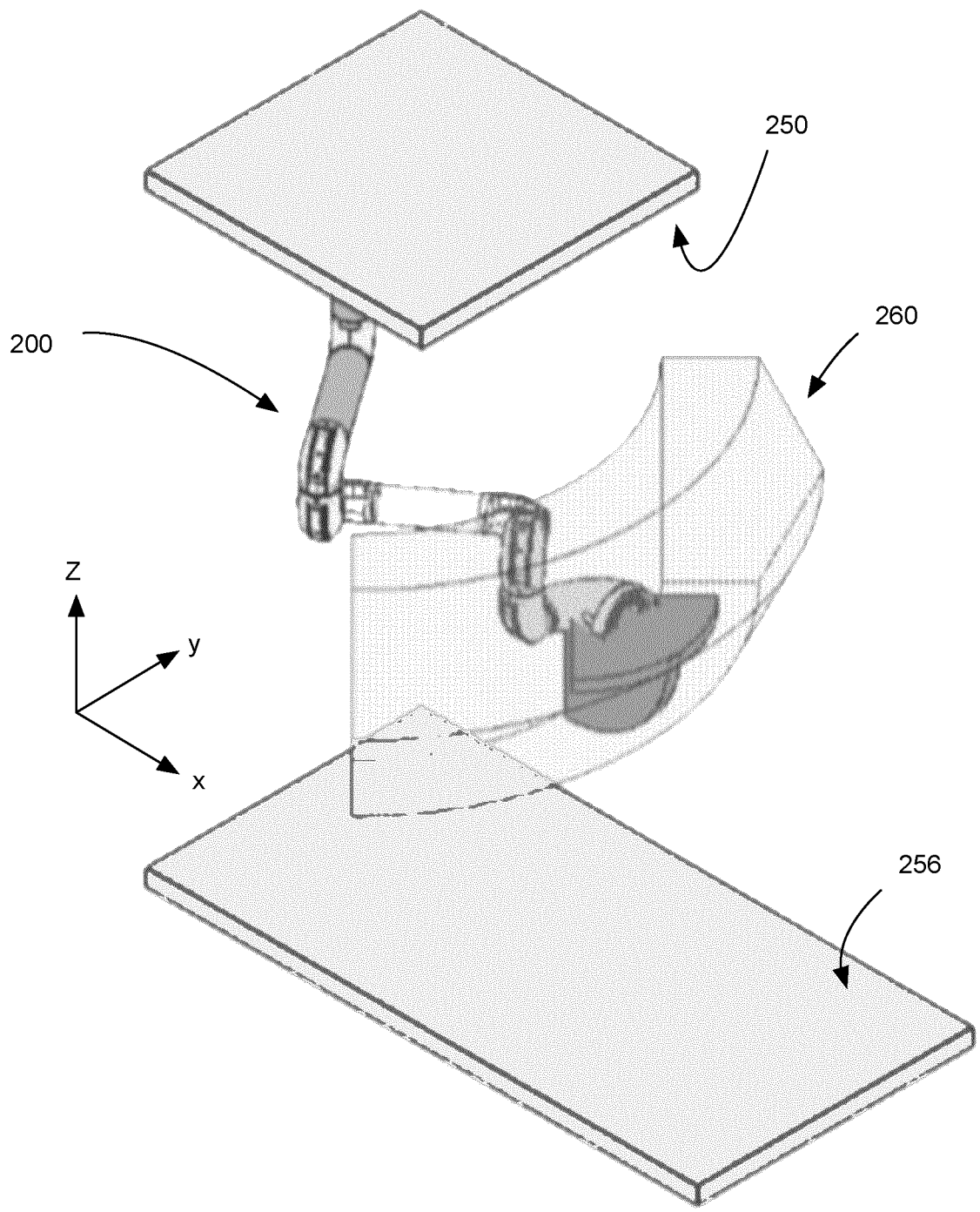
FIG. 11 is a perspective schematic view of the operating range of the lighting system of FIGS. 5A to 6.

FIGS. 11 and 12A to 12C show the dimensions and operating range of the lighting system 200 of FIGS. 5A to 6. In particular, FIG. 11 shows the operating range 260 of the lighting structure 204 relative to the ceiling 250 and a floor 256. The lighting structure 204 is articulable via the lighting support structure 212 through a range of 90 degrees about a vertical axis z, thus movable through a range of 82 inches horizontally, and can be extended between 35 and 55 inches from a pivot axis PA extending along the vertical axis z. Additionally, the lighting structure 204 can be rotated 90 degrees relative to a horizontal axis HA, and extended between 31 and 65 inches from the ceiling 250.

The lighting systems can be disassembleable for cleaning. In addition, a fogging procedure can be employed daily or at some other desired frequency to disinfect the device.

While, in the above-described embodiments, the light-emitting elements are light-emitting diodes, any other suitable light-emitting element can be employed.

In other embodiments, the lighting system can be configured to be secured to a wall or rest on a floor, with the output end being connected to a vacuum system.

In another embodiment, a simple vacuum system can be used, wherein the air is expelled in a region that is generally unoccupied or traversed by humans and/or animals.

In a further embodiment, a vacuum system can be at least partially positioned within the lighting support structure.

The lighting system is designed to facilitate disassembly for cleaning as desired.

In other embodiments, the articulation damping structure can be external of the air conduit or can be omitted altogether. In one alternative embodiment, sufficient compressive forces can be conditionally applied at the joints to provide friction to resist reorientation once the configuration of the lighting system is set. In another alternative embodiment, ratcheted joints can be employed, requiring a minimum threshold force to rotate the support structure sections relative to one another.

Although specific advantages have been enumerated above, various embodiments may include some, none, or all of the enumerated advantages.

Persons skilled in the art will appreciate that there are yet more alternative implementations and modifications possible, and that the above examples are only illustrations of one or more implementations. The scope, therefore, is only to be limited by the claims appended hereto and any amendments made thereto.

What is claimed is:

1. A lighting system with vacuum intake, comprising:
a lighting structure including at least one light-emitting element dimensioned to illuminate a region;
a lighting support structure extending at a first end thereof from the lighting structure and enabling repositioning of the lighting structure relative to a second end of the lighting support structure, the lighting support structure having an air conduit extending therealong and connectable or connected towards the second end of the lighting support structure to a vacuum system, the air conduit being in fluid communication with a vacuum intake positioned towards the lighting structure, wherein the lighting support structure has an articulating arm formed from at least a first support structure section and a second support structure section that articulate relative to each other at a joint, to enable rotation the first support structure section relative to the second support structure section, the first support structure section comprising a first electrical contact, the second support structure section comprising a second electrical contact, wherein the first electrical contact remains in continuous electrical communication with the second contact during said repositioning.

2. The lighting system with vacuum intake of claim 1, wherein the at least one light-emitting element incudes at least one light-emitting diode.

3. The lighting system with vacuum intake of claim 1, wherein the lighting structure is positioned to at least partially surround the vacuum intake.

4. The lighting system with vacuum intake of claim 3, wherein the lighting structure fully surrounds the vacuum intake.

5. The lighting system with vacuum intake of claim 1, further comprising a vacuum system in fluid communication with the air conduit towards the second end of the lighting support structure.

6. The lighting system with vacuum intake of claim 1, further comprising an electrical wiring guide system positioned within the air conduit to guide electrical wiring from the lighting structure through the lighting support structure.

7. The lighting system with vacuum intake of claim 1, further comprising an articulation damping system connected to the lighting support structure to resist articulation of the lighting support structure.

8. The lighting system with vacuum intake of claim 7, wherein the articulation damping system is positioned in the air conduit of the lighting support structure.

9. The lighting system with vacuum intake of claim 1, wherein the lighting support structure includes at least two support structure segments, and a rotational joint between a first of the at least two support structure segments and a second of the at least two support structure segments.

10. The lighting system with vacuum intake of claim 9, further comprising an articulation damping system connected to the lighting support structure to resist articulation of the first of the at least two support structure segments and the second of the at least two support structure segments.

11. The lighting system with vacuum intake of claim 10, wherein the articulation damping system is positioned in the air conduit of the lighting support structure.

12. The lighting system with vacuum intake of claim 10, further comprising an electrical guide system positioned within the air conduit to guide electrical wiring from the lighting structure through the lighting support structure.

13. The lighting system with vacuum intake of claim 1, further comprising a booster fan positioned within the lighting support structure.

14. The lighting system with vacuum intake of claim 1, further comprising a bag filter fitted within the vacuum intake.

15. The lighting system with vacuum intake of claim 1, suitable for use in a healthcare facility to simultaneously illuminate the oral region of a patient and to remove airborne particles expelled by the patient.

\* \* \* \* \*